United States Patent
Gates et al.

(10) Patent No.: US 12,011,513 B1
(45) Date of Patent: Jun. 18, 2024

(54) APPARATUS AND METHOD FOR DECONTAMINATING AN ENCLOSED SPACE

(71) Applicant: AMERICAN WATER PURIFICATION, INC., Wichita, KS (US)

(72) Inventors: Danny Eugene Gates, Wichita, KS (US); James Edward Loewen, Wichita, KS (US)

(73) Assignee: AMERICAN WATER PURIFICATION, INC., Wichita, KS (US)

(*) Notice: Subject to any disclaimer, the term of this patent is extended or adjusted under 35 U.S.C. 154(b) by 568 days.

(21) Appl. No.: 17/243,293

(22) Filed: Apr. 28, 2021

Related U.S. Application Data

(60) Provisional application No. 63/016,833, filed on Apr. 28, 2020.

(51) Int. Cl.
*A61L 2/20* (2006.01)
*A61L 2/24* (2006.01)
*A61L 101/02* (2006.01)

(52) U.S. Cl.
CPC ............... *A61L 2/24* (2013.01); *A61L 2/202* (2013.01); *A61L 2101/02* (2020.08); *A61L 2202/11* (2013.01); *A61L 2202/14* (2013.01); *A61L 2202/15* (2013.01); *A61L 2202/16* (2013.01); *A61L 2202/25* (2013.01)

(58) Field of Classification Search
CPC ........ A61L 2/24; A61L 2/202; A61L 2101/02; A61L 2202/11; A61L 2202/14; A61L 2202/15; A61L 2202/16; A61L 2202/25
USPC ....................................................... 422/105
See application file for complete search history.

(56) References Cited

U.S. PATENT DOCUMENTS

| | | |
|---|---|---|
| 9,186,428 B2 | 11/2015 | Jennings |
| 2003/0086813 A1 | 3/2003 | Fleischer |
| 2005/0031486 A1 | 2/2005 | Mole et al. |
| 2008/0310992 A1 | 12/2008 | Heselton et al. |
| 2012/0063949 A1* | 3/2012 | Jennings ............... F24F 8/26 422/295 |

* cited by examiner

*Primary Examiner* — Huy Tram Nguyen
(74) *Attorney, Agent, or Firm* — Robert O. Blinn

(57) ABSTRACT

A decontamination system employs at least one ozone generator located within an enclosed space, at least one ozone sensor and a control system for controlling the operation of the at least one ozone. During a decontamination cycle, the at least one ozone generator is operated to disperse ozone within the enclosed space until the at least one ozone sensor indicates that a desired decontamination ozone level has been reached.

1 Claim, 7 Drawing Sheets

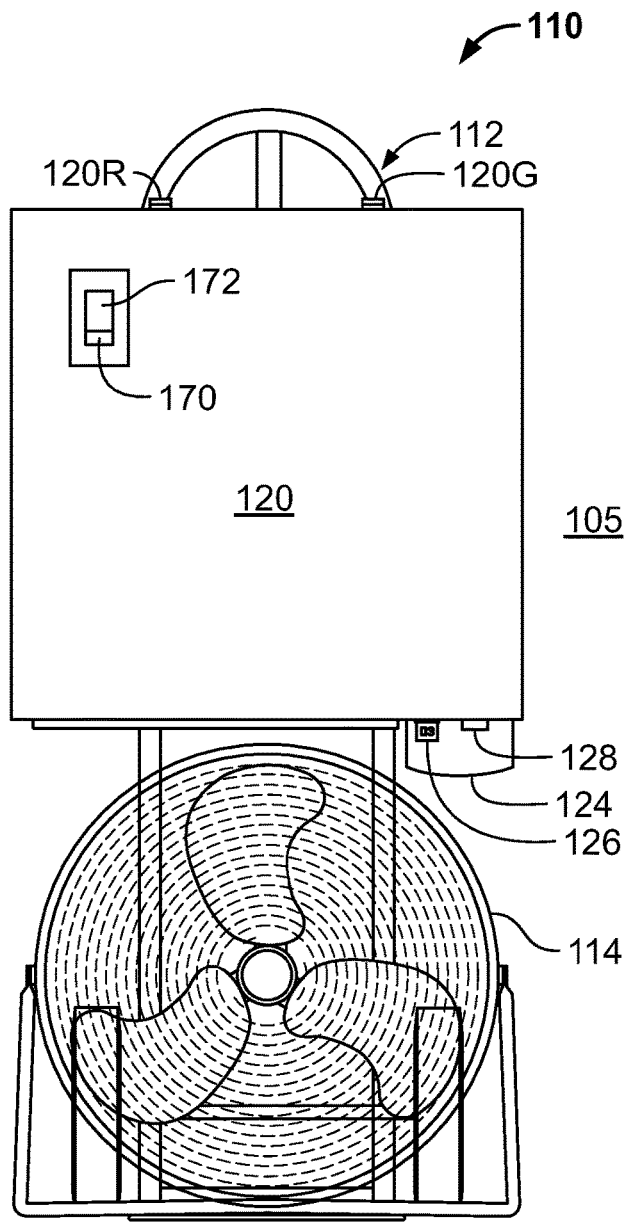
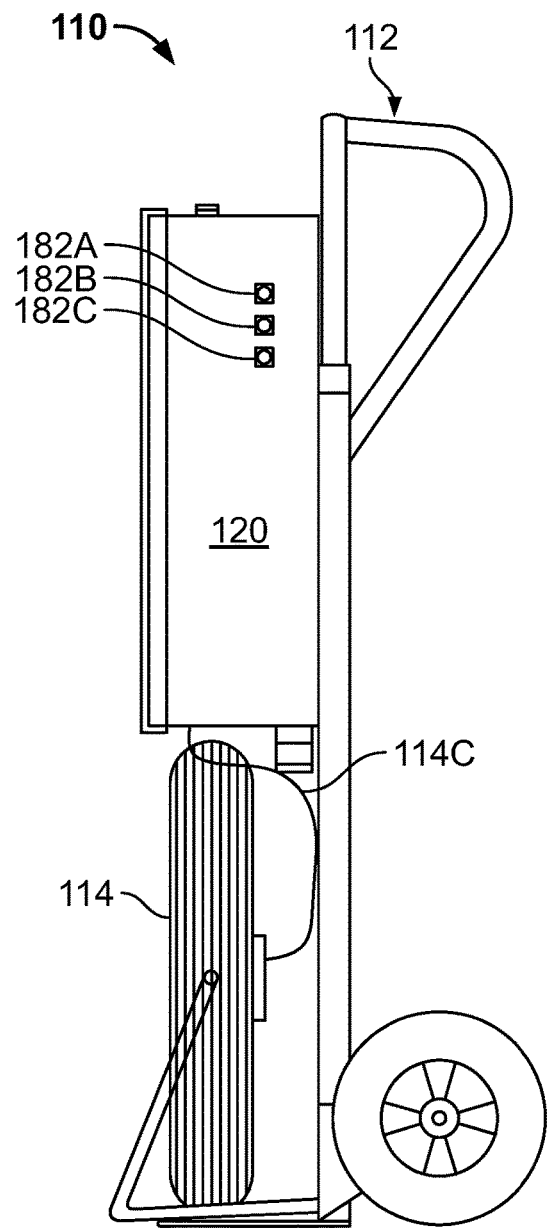
FIG. 4
FIG. 5

INITIATION SEQUENCE A

(a) Key card 192 is inserted into card receiver 192. (b) Motion detection bypass switch 172 has been activated and that activation occurred a pre-selected period of time in the past. (c) Motion detector 170 is not detecting motion. (d) At least one ozone generator board switch is in the on position. If (a) - (d) true then go to Operation Sequence B

FIG. 10A

OPERATION SEQUENCE B

(a) Power to all fans. (b) power to selected ozone generator boards (c) power to red light 120R (d) Monitor ozone sensor (i) If ozone is above 0.1 ppm, power to blue strobe light 124, (ii) If ozone is not above 2.5 ppm after 30 minutes of operation, red light 120R on, GO TO SHUTDOWN SEQUENCE (iii) if ozone > 4ppm, GO TO SHUTDOWN SEQUENCE C

FIG. 10B

SHUTDOWN SEQUENCE C

(a) Shut off power to ozone generators. (b) If ozone < 0.1PPM, then, (i) shut off power to all fans and all lights and turn green light 120G on in a steady, non-blinking mode

FIG. 10C

APPARATUS AND METHOD FOR DECONTAMINATING AN ENCLOSED SPACE

RELATED APPLICATIONS

This application claims the benefit of U.S. Provisional Patent Application No. 63/016,833 which was filed on Apr. 28, 2020, which is incorporated herein by reference in its entirety.

FIELD

This invention relates to an apparatus and method for conditioning the air in an enclosed space with the purpose of decontaminating the air within the enclosed space as well as objects and surfaces that are within the enclosed space with the object of destroying viruses and bacteria.

BACKGROUND

Enclosed spaces, particularly enclosed public spaces are in need of decontamination or disinfecting with the object of effectively destroying viruses and bacteria that may be within an enclosed space either in the air or on surfaces within the enclosed space. What is needed is a system and method for causing a gaseous disinfecting agent to flow into and within such an enclosed space in order to cause such a destruction of viruses and bacteria.

SUMMARY

The above described need is addressed by an apparatus and method that is adapted for introducing ozone into an enclosed space such that the ozone concentration reaches a predetermined level. The decontamination system employs at least one ozone generator located within an enclosed space, at least one ozone sensor for measuring ozone concentration within the enclosed space and a control unit for controlling the operation of the at least one ozone generator. During a decontamination cycle, the at least one ozone generator device is operated to disperse ozone within the enclosed space until the at least one ozone sensor indicates that a desired ozone level has been reached. When the desired ozone level is reached, the control unit shuts down the at least one ozone generator. Because ozone is unstable and has a half-life of approximately 20 minutes, the ozone typically disperses within the enclosed space within a sufficiently short period of time to allow decontamination within an enclosed space during spans of time when the enclosed spaced is not occupied.

BRIEF DESCRIPTION OF THE DRAWINGS

FIG. 4 is a front view of a second embodiment of a decontamination apparatus which is a portable decontamination apparatus.

FIG. 5 is a side view of the second embodiment portable decontamination apparatus.

FIG. 10A illustrates the logic that controls the initiation sequence portion of the operation of the second embodiment portable decontamination apparatus.

FIG. 10B illustrates the logic that controls the operation sequence portion of the operation of the second embodiment portable decontamination apparatus.

FIG. 10C illustrates the logic that controls the shutdown sequence portion of the operation of the second embodiment portable decontamination apparatus.

DETAILED DESCRIPTION

Figure 1:
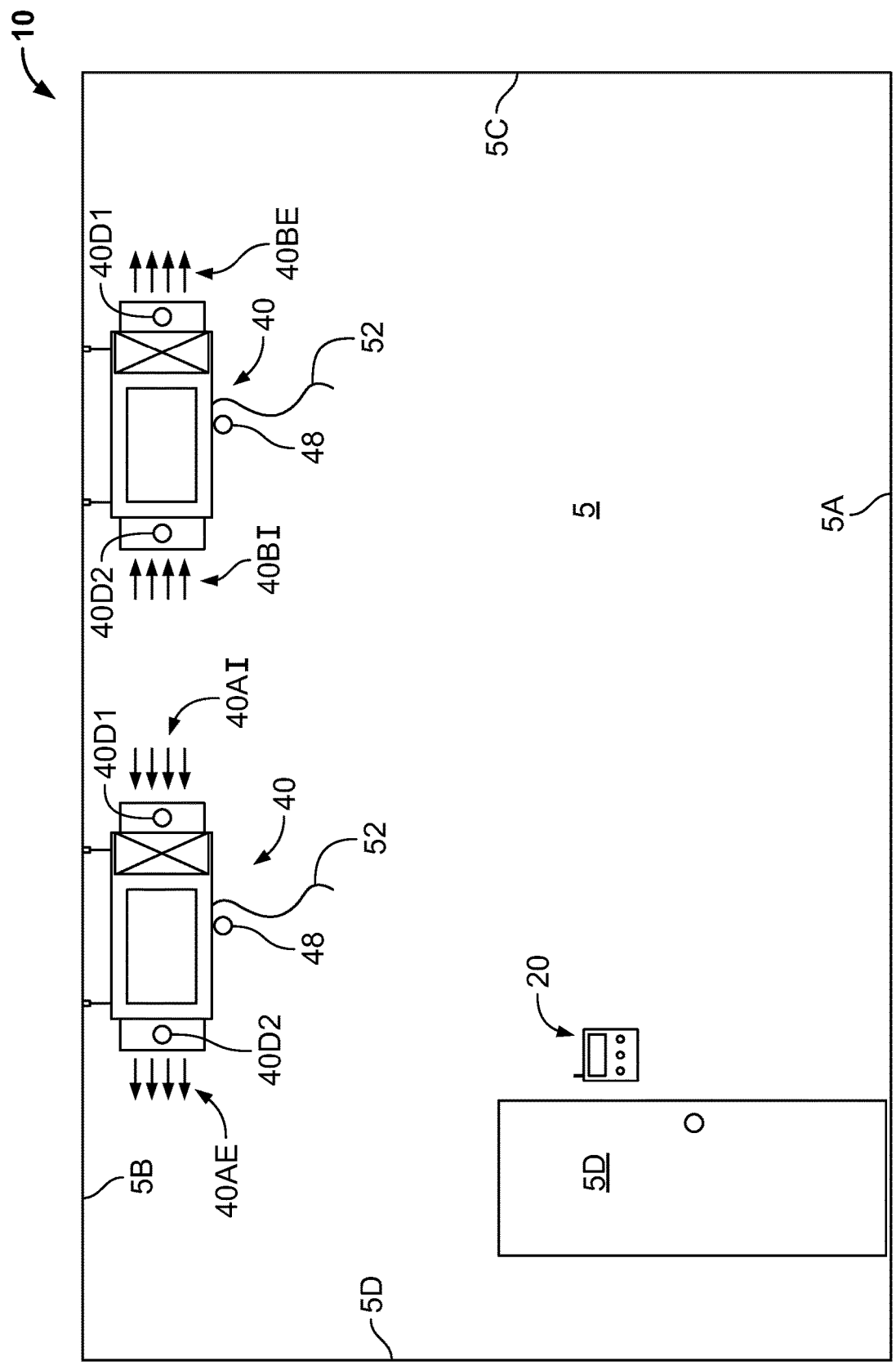
FIG. 1 is a schematic diagram of a first embodiment of a decontamination apparatus for use in a room which is an enclosed volume of space.

Referring to the figures, FIG. 1 provides a schematic diagram of one embodiment of a decontamination system 10. As can be seen in FIG. 1, decontamination system 10 is arranged for use for decontaminating a room 5 which is indicated schematically as an enclosed space. As shown in FIG. 1, room 5 is bounded by floor 5A, a ceiling 5B and a plurality of walls 5C. In this example, room 5 also includes at least one entry and exit door 5D. The skilled reader is to understand that room 5 may be any enclosed volume of space that is typically occupied by people either for business, retail commerce, work, or entertainment or for virtually any purpose that results in the presence of people within room 5. It is contemplated that room 5 is not utilized at all hours of the day and night as would be the case with a residence. It is envisioned that room 5 would not be in use and therefor would be vacant during a portion of the day or night during a vacant period as might be the case with an office, a restaurant or theater or the like. It is during such a vacant period that the applicant envisions decontamination system 10 being operated.

As can be seen in FIG. 1 decontamination system 10 includes a control unit 20 and at least one ozone generator and ozone destruct unit 40. As can be seen in FIG. 1, two ozone generator and destruct units 40 are shown. However, one or more such units may be included in decontamination system 10 depending on the size and use of room 5. As can be seen in FIG. 1, control unit 20 is preferably mounted adjacent to door 5D. Moreover, as can be seen in FIG. 1, both of the ozone generator and destruct units 40 are preferably mounted to ceiling 5B in an evenly spaced manner.

Figure 2:
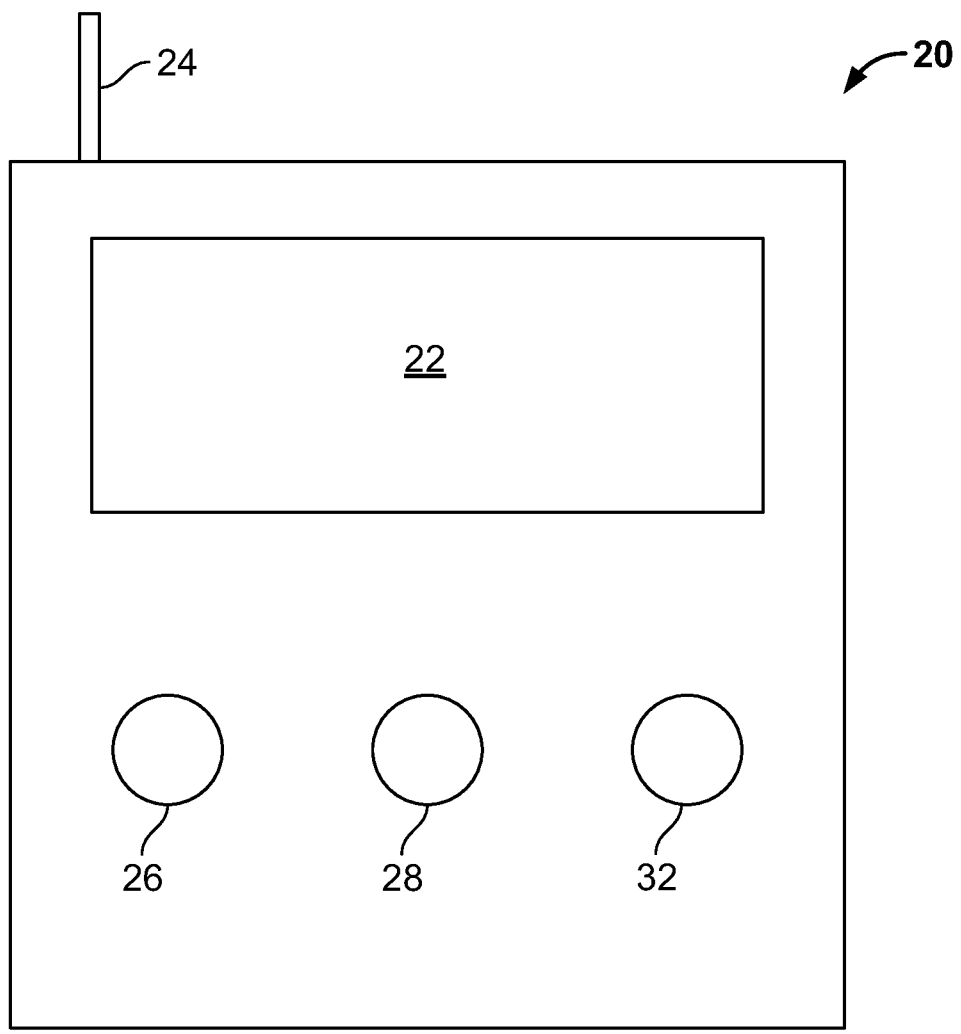
FIG. 2 is a magnified view of the control unit shown in FIG. 1.

As can be seen in FIG. 1, control unit 20 is preferably mounted adjacent to door 5D. A magnified view of control unit 20 is provided in FIG. 2. As can be seen in FIG. 2, control unit 20 may include a central processing unit (not shown), a display screen 22, a wireless antenna 24 for communication with other units as will be described below, an on off control switch 26, an emergency stop switch 28 and a combination red and green light 32. Display screen 22 may be arranged to display such things as operating status, run time and any alarms that may be occurring. Light 32 is arranged to display a green light when decontamination system 10 is not operating and when ozone levels in room 5 are at or below a level that is deemed safe for human occupancy. In this example, light 32 could display a red light when decontamination system 10 is operating or when ozone levels in room 5 are above a predetermined level above which it is not recommended for people to be within room 5. Control unit 20 is adapted for wirelessly receiving data from and sending operation control commands to the at least one ozone generator and destruct unit 40 as will be described in greater detail below.

Figure 3:
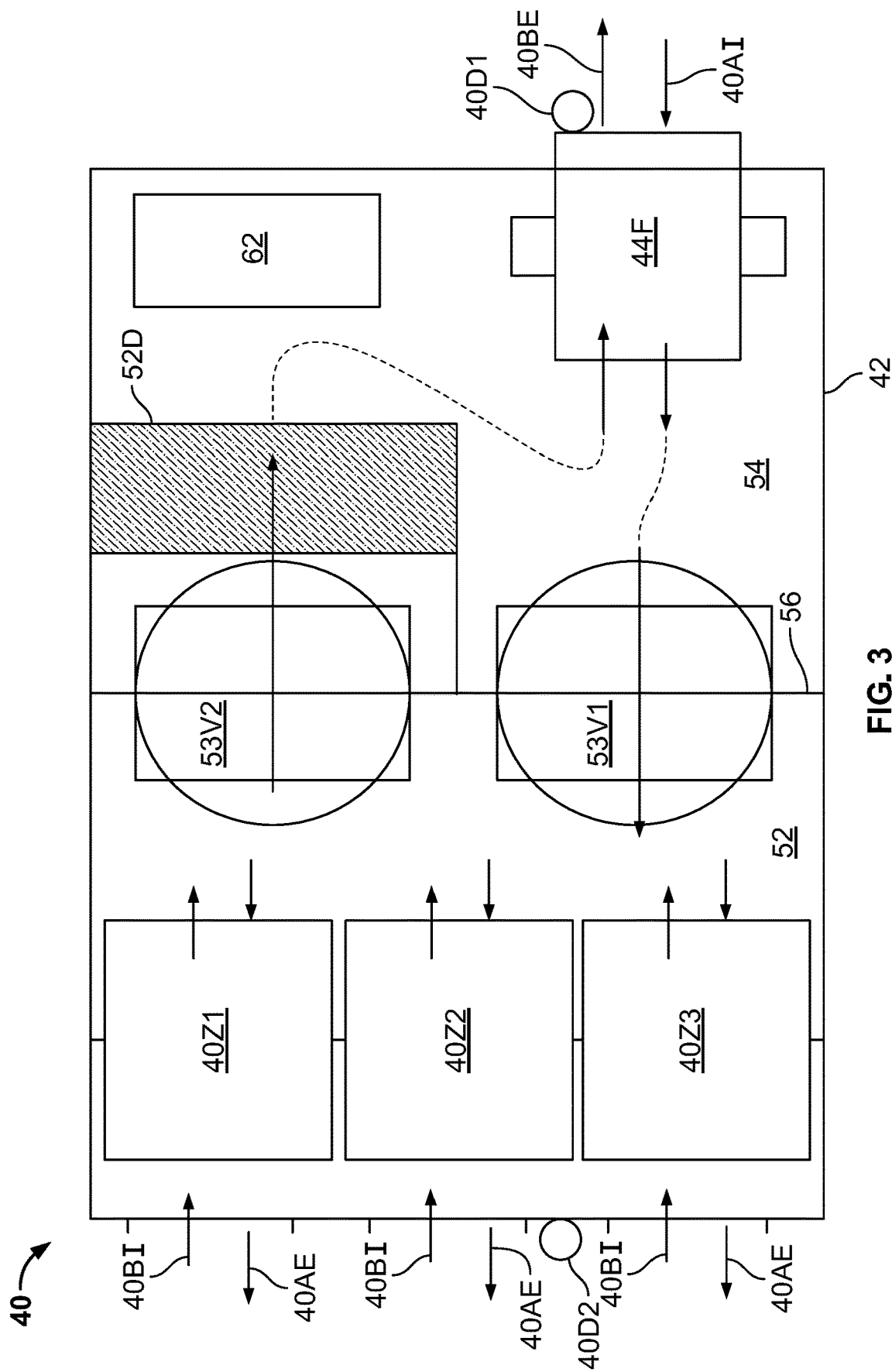
FIG. 3 is a detailed schematic view of an ozone generator and ozone destruct device for use in the first embodiment decontamination system.

Ozone generator and destruct unit 40 is shown in greater detail in FIG. 3. Ozone generator and destruct unit 40 is controlled by a control module 62. The allocation of tasks between control unit 20 and control module 62 is a matter of preference as will be discussed in further detail below. Ozone generator and destruct unit 40 is configured to run in two modes: a first ozone generating mode and a second ozone destruct mode. As can be seen in FIG. 3, ozone generator and destruct unit is arranged in an enclosed case 42 which is, in turn, divided by a wall 56 into an ozone generator chamber 52 and an ozone destruct chamber 54. Wall 56 presents two one-way flap valves: ozone generator feed valve 53V1 and ozone destruct feed valve 53V2. Both ozone generator feed valve 53V1 and ozone destruct feed valve 53V2 are one way flap valves that restrict the flow of air as indicated by the flow arrows superimposed over the valves in FIG. 3. A two-way fan 44F that is mounted within wall 42 common to chamber 54 either pushes air through ozone generator feed valve 53V1 or pulls air through ozone destruct valve 53V2. The air flow indicated a 40AI and 40AE in FIGS. 1 and 3 is indicative of the ozone generating mode. The air flow indicated a 40BI and 40BE in FIGS. 1 and 3 is indicative of the ozone destruct mode. FIG. 1 shows both flow directions for the two ozone generators and destruct units 40 shown in FIG. 1. This is done in FIG. 1 purely for illustrative purposes. In almost any mode of operation for system 10, in a system having two ozone generators and destruct units 40, both or all units 40 would be in the same one of three possible states (a) all not running or (b) all running in the ozone generator mode (with flow 40AI and 40AE) or (c) all running in the ozone destruct mode (with flow 40BE and 40BI).

As can be seen in FIG. 3, ozone destruct chamber contains a catalyst cartridge 52D. Catalyst cartridge 52D of a type that is well known in the art that is adapted for capturing and neutralizing ozone as air flows through the cartridge. Catalyst cartridge 52D is arranged so that air that is drawn though ozone destruct feed valve 53V2 passes exclusively through catalyst cartridge 52D and from cartridge 52D into chamber 54 to be exhausted by fan 44F as air flow 40BE.

To operate ozone generator and destruct unit 40 in the ozone generating mode, fan 44F is activated to push inlet air 40AI into chamber 54 and ozone generator units 40Z1, 40Z2 and 40Z3 are activated. But that air exits chamber 54 through ozone generator feed valve 53V1 into ozone generator chamber 52 and does not pass through catalyst cartridge 52D. The air flowing into ozone generator chamber 52 passes through the operating ozone generators 40Z1, 40Z2 and 40Z3 before it exits into room 5 as ozone enriched air via air flows 40AE.

In order to operate ozone generator and destruct unit 40 in the ozone destruct mode, ozone generators 40Z1, 40Z2 and 40Z3 are all turned off and fan 44F is activated to pull inlet air 40BI through the dormant ozone generators into chamber 52. From ozone generator chamber 52, the ozone laden air passes exclusively through ozone destruct feed valve 53V2 and exclusively into ozone destruct catalyst cartridge 52D. As the airstream passes through ozone destruct catalyst cartridge 52D, ozone in the air stream is absorbed and captured. The ozone depleted air flowing out of ozone destruct cartridge 52D is then exhausted by two-way fan 44F as an ozone depleted air stream 40BE.

As can also be seen in FIG. 3, ozone generator and destruct unit 40 is provided with ozone sensors 40D1 and 40D2. Whichever ozone sensor is at the inlet to ozone generator and destruct unit 40 depending on the direction of operation of fan 44F, provides a measurement of the ozone concentration in room 5. During the ozone generation phase, the measurement of ozone concentration given by sensor 40D1 is used by control unit 20 (or control module 62) to establish and maintain the ozone concentration within room 5 within a desired pre-determined range for a desired period of time. During the ozone destruct phase, ozone sensor 40D2 provides measurements to control unit 20 for determining when the level of ozone concentration entering unit 40 has reached a predetermined desired low level.

If room 5 has a relatively small volume, a single ozone generator and destruct unit 40 may be sufficient for treating that volume of air. However, if the volume of room 5 may be sufficiently large to require two or more ozone generator and destruct units 40. In this example, ozone generator and destruct unit 40 may include ozone generators like or similar to 0-555 Enerzen (R) ozone generator which can be obtained from Clean Living Solutions, Inc. of Houston, Texas for from ION Technologies of Houston, Texas, or could incorporate such an ozone generator or could be similar to such an ozone generator. Catalyst cartridge 52 may also be of a type well known in the art.

In this example, ozone generator and destruct unit 40 is preferably mounted to ceiling 5B by mount members 40M. As can be seen in FIG. 1, ozone generator and destruct unit 40 may also be provided with a motion detector 48 on its lower surface. A ceiling mounted unit such as ozone generator and destruct unit 40 provides a suitable location for such a motion detector.

Ozone generator and destruct unit 40 is also provided with suitable controls and wireless communication capability via an antenna 52 all being of types well known in the art for communication with control unit 20. More particularly, the wireless communication portion of ozone generator and destruct unit 40 is adapted to receive a first activation signal from control unit 20 for activating the operation of ozone generators as described above and a second de-activation signal from control unit 20 for ceasing operation of ozone generators as noted above. Still further, the wireless communication portion of ozone generator and destruct unit 40 is able to send signals via antenna 52 to control unit 20 at pre-determined intervals that provide the level of ozone concentration detected by the ozone concentration sensors. Even still further, the wireless communication portion of ozone generator and destruct unit 40 is able to send signals via antenna 52 to control unit 20 should motion detector 48 detect any motion within room 5.

An optional configuration for ozone generator and destruct units 40 would include a red and green light such as red and green light 32 that is mounted on control unit 20 may also be or in the alternative be mounted on the lower surface of ozone generator and destruct unit 40. A siren or horn or other noise making device (not shown) for issuing warnings could also be integrated in ozone generator and destruct unit 40. Still further, the functions of control module 62 may be adapted such that control unit 20 would initiate a decontamination cycle while control module 62 would manage all other phases of the operation of one or more ozone generator and destruct units 40 as described herein.

The operation of decontamination system 10 is intended to occur at times when no people are present in room 5. Accordingly control unit 20 is arranged to initiate operation and to permit operation when no motion is being detected by any one of motion detectors 48 associated with the at least one ozone generator 40 and the at least one ozone destruct unit 70 respectively. Preferably, control unit 20 includes a key system for inputting a passcode to thereby limit operation to only authorized personnel. Once the preferable passcode is entered, on button 26 may be pressed, preferably as the operator exits room 5 via door 5D. Preferably, upon activation, control unit 20 activates warning signals such as, for example, a flashing red light from light 32 and an audible horn or other noise making device that further warns the operator to leave room 5. In one preferred system, the flashing red light of light 32 flashes during the entire period of time when unacceptably high levels of ozone are present for human respiration and the noise device will sound as a warning to exit room 5.

The operation of decontamination system 10 by control unit 20 or in concert with or in the alternative control module 62 further includes a series of steps such that when, during operation, motion is detected by one of motion detectors 48, the sole or all ozone generators within ozone generator and destruct units 40 (depending on the size of the system and the quantity of ozone generators 40 in the system) are turned off and the ozone destruct mode is activated as described above to quickly reduce the concentration of ozone in room 5.

During normal operations, the ozone generators of ozone generator and destruct unit 40 will be controlled by control unit 20 (or control module 62) as it receives ozone concentration readings from sensor 40D1 to continue operating until a predetermined ozone concentration is reached within room 5. In the alternative, control module 62 could receive sensor readings from sensor 40D1 and control the operation of ozone generator and destruct unit 40. In this example, the predetermined ozone concentration that would preferably be reached could be approximately 40 ppm. But, this is just an example minimum level for decontamination. In some instances, in some applications, the desired minimum level could be much lower or even higher. An example effective range may be between 40 ppm and 50 ppm Ozone, so that, in this example 40 ppm would represent a "predetermined lower limit value" and 50 ppm would represent a "predetermined upper limit value". In this example, control unit 20 (or in the alternative control module 62) could be configured, so that during a span of time when decontamination was in progress, control unit 20 or control module 62 would cause the ozone generators 40Z1, 40Z2 and 40Z3 to be deactivated if ozone levels are measured to be above the upper limit value and would cause ozone generators 40Z1, 40Z2 and 40Z3 to resume operation if ozone levels fell to or below the lower limit value. Control unit 20 or control module 62 would also be configured to maintain such ozone levels as described above for a pre-determined desired period of time that is deemed to be an effective period of time for decontamination at the selected range of ozone concentrations.

After a decontamination cycle within the desired ozone concentration range has been conducted for the desired period of time, the system will be controlled to switch to the ozone destruct mode. Ozone generators 40Z1, 40Z2 and 40Z3 are shut down and the flow of air through ozone generator and destruct unit 40 is reversed as described above in order to pull air from room 5 through catalyst cartridge 52D. Although air from room 5 does initially pass though ozone generators 40Z1, 40Z2 and 40Z3 into chamber 52, because ozone generators 40Z1, 40Z2 and 40Z3 are shut down, they do not introduce any ozone into the incoming air. Control unit 20 or control module 62 receives signals from ozone sensor 40D2 in order to monitor the level of ozone in the air that is entering ozone generator and destruct unit 40. Eventually, as air from room 5 is passed though ozone destruct catalyst cartridge 52D, the ozone level in the air will be reduced. When the ozone levels in the incoming air as measured by ozone sensor 40D2 falls to a predetermined level, control unit 20 or control module 62 will shut down the system and reset to await the next decontamination cycle.

As can be seen from the above description, decontamination system 10 provides an effective automated apparatus for decontaminating a room 5 of an effective portion of bacteria and viruses that may have been present in room 5. Decontamination system 10 may be used most effectively in enclosed public and business spaces that are intermittently unoccupied. Such spaces would include restaurant dining rooms that are unoccupied and not used during late night and early morning hours. Offices, theaters, retail spaces and commercial kitchens may also be examples of spaces that are unoccupied for significant periods of time between daily uses. All such enclosed spaces might be appropriate for treatment by a system such as decontamination system 10 as described above to thereby impede the spread of potentially dangerous pathogens.

A second embodiment decontamination unit 110 for dispersing ozone in an enclosed space 105 (indicated in FIG. 4) is shown in FIGS. 4-9. Decontamination unit 110 is a portable unit. As can be seen in FIGS. 4 and 5, decontamination unit 110 includes a mobile support portion 112, a circulation fan 114 and an ozone generator cabinet 120. In this example, the means for transporting decontamination unit 110, namely mobile support portion 112 is a hand truck or dolly. However, any suitable wheeled cart or other suitable mobile platform that is able to be manually moved and maneuvered would provide suitable mobility for portable decontamination unit 110. A hand truck has been chosen for this example, because the upright configuration shown in FIGS. 4 and 5 is suitable for easily storing or transporting a plurality of decontamination units 110 within a limited space. As can be seen in FIG. 4, the front panel of cabinet 120 presents a motion detector 170 and a motion detector bypass switch 172. The operation of motion detector 170 and motion detector bypass switch 172 will be described below.

As can be seen in FIG. 5, the right side panel of cabinet 120 presents three switches, ozone generator board switch 182A, ozone generator board switch 182B and ozone generator board switch 182C. The operation of these ozone generator board switches will be described below.

Figure 6:
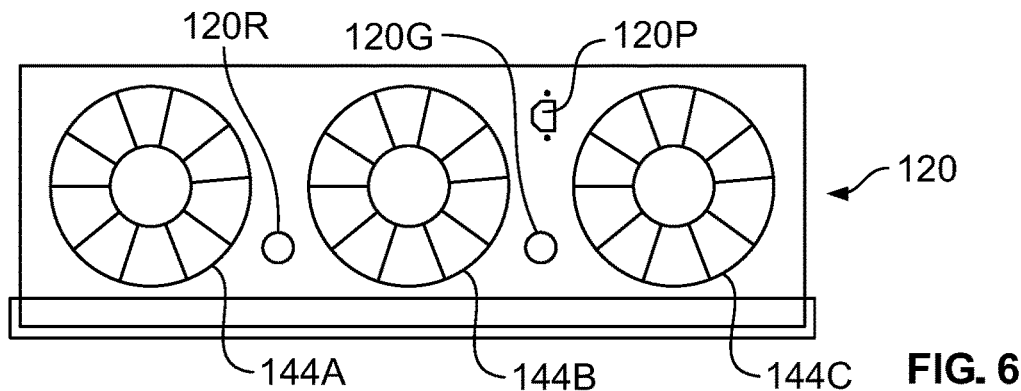
FIG. 6 is a top view of the ozone generator cabinet of the second embodiment portable decontamination apparatus.
Figure 7:
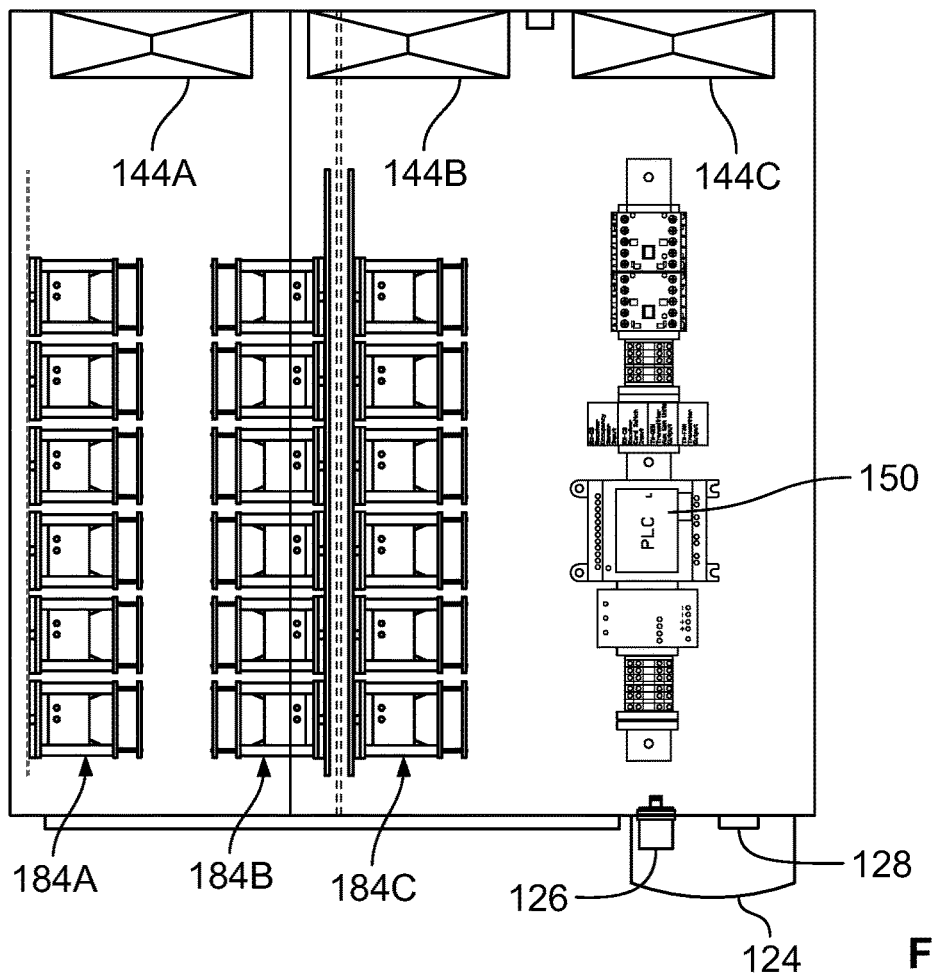
FIG. 7 is a front view of the ozone generator cabinet of the second embodiment portable decontamination apparatus with the front panel of the cabinet removed to show its internal components.
Figure 8:
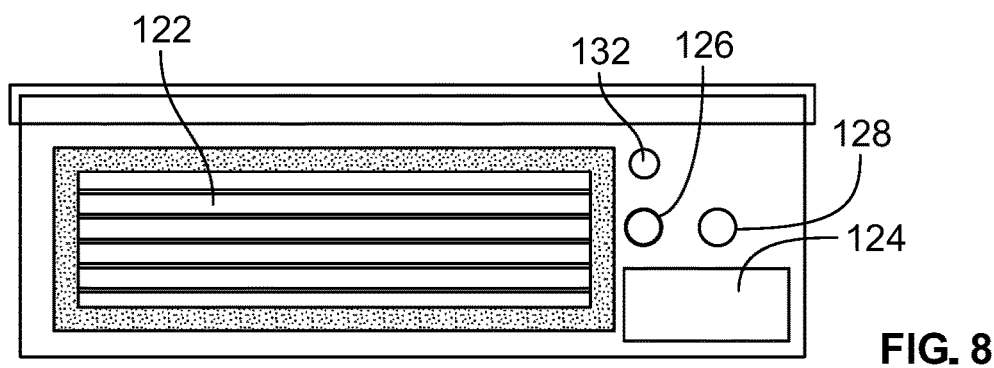
FIG. 8 is a bottom view of the ozone generator cabinet of the second embodiment portable decontamination apparatus.

Ozone generator cabinet 120 is further illustrated in FIGS. 6-8. FIG. 8, which is a top view of cabinet 120, shows an air intake structure 122. Also, in FIG. 6, in this bottom view, there are shown a blue strobe light 124, an ozone sensor 126, and a fan chord opening 132 which provides a passageway for a power chord 114C (shown in FIG. 5) which provides power to recirculation fan 114. The operation of blue strobe light 124 and ozone sensor 126 will be also described below. A buzzer 128 is also located on the bottom surface of cabinet 120. Generally, buzzer 128 is activated when decontamination unit 110 is operating and motion is detected by motion sensor 170.

FIG. 8, which is a top view of cabinet 120, shows three axial exhaust fans 144A, 144B and 144C. Axial exhaust fans 144A, 144B and 144C are suitable for pulling air into cabinet 120. When the ozone generator boards are operating, air is drawn into cabinet 120 through air intake structure 122 and ozone laden air is exhausted by exhaust fans 144A, 144B and 144C out though the top of cabinet 120. In this example, the applicants selected 182 CFM axial fans for each of exhaust fans 144A, 144B and 144C.

As can also be best seen in FIG. 8, the top surface of cabinet 120 presents a power inlet fitting 120P, which in this example, is a male three prong connector suitable for connecting to a standard three prong 110V extension cord. Also, as shown in FIG. 6, a red light 120R and a green light 120G are mounted to the top surface of cabinet 120.

FIG. 7, is a front view of cabinet 120, with cabinet 120 opened to expose the components within cabinet 120. Cabinet 120 houses three ozone generator boards, 184A, 184B and 184C. Each ozone generator board, in this example, includes 6 ozone generator modules. Each ozone generator module includes an intake, a fan, an ozone generator portion and an outlet. Each ozone generator module may be any one of several ozone generator modules that are commercially available and well known to those who are skilled in the art. In this example, the applicants have chosen a 2 plate 10 g/hr Ozone Generator from Shenzhen Shuyi Electronics Co. Ltd. for each of the six ozone generator modules in each ozone generator board. In this example, ozone generator board control switches 182A, 182B and 182C noted above are for enabling the operation of ozone generator boards 184A, 184B and 184C respectively. In this example, any one of, or two of or all of ozone generator boards 184A, 184B and 184C may be enabled by toggling a corresponding one of or combination of ozone generator board control switches 182A, 182B and 182C which are shown in FIG. 5 into an "on" position. In this example, the applicants estimate that each ozone generator board would be able to generate sufficient ozone for efficiently decontaminating an enclosed space having floor space of approximately 500 square feet.

As can be seen in FIG. 7, a Programmed Logic Control (PLC) unit 150 is located is located inside cabinet 120. The operation of PLC unit 150 will be described below.

The skilled reader will appreciate that, for clarity, FIG. 7 does not show the many wires that would be needed to transfer signals from switches, detectors and sensors to PLC unit 150 or which provide power to all of the various components. Further, FIG. 7 does not detail ordinary design aspects such as a power distribution arrangement, which, accordingly to what is well known in the art, would include power relay switches and the like for providing power to various components (e.g. ozone generator boards, the various fans, the blue strobe light and other lights which are described above). In accordance with what is known by those who is skilled in the art, power relay switches would be provided that could be activated by the PLC unit to provide power to various selected components.

Figure 9:
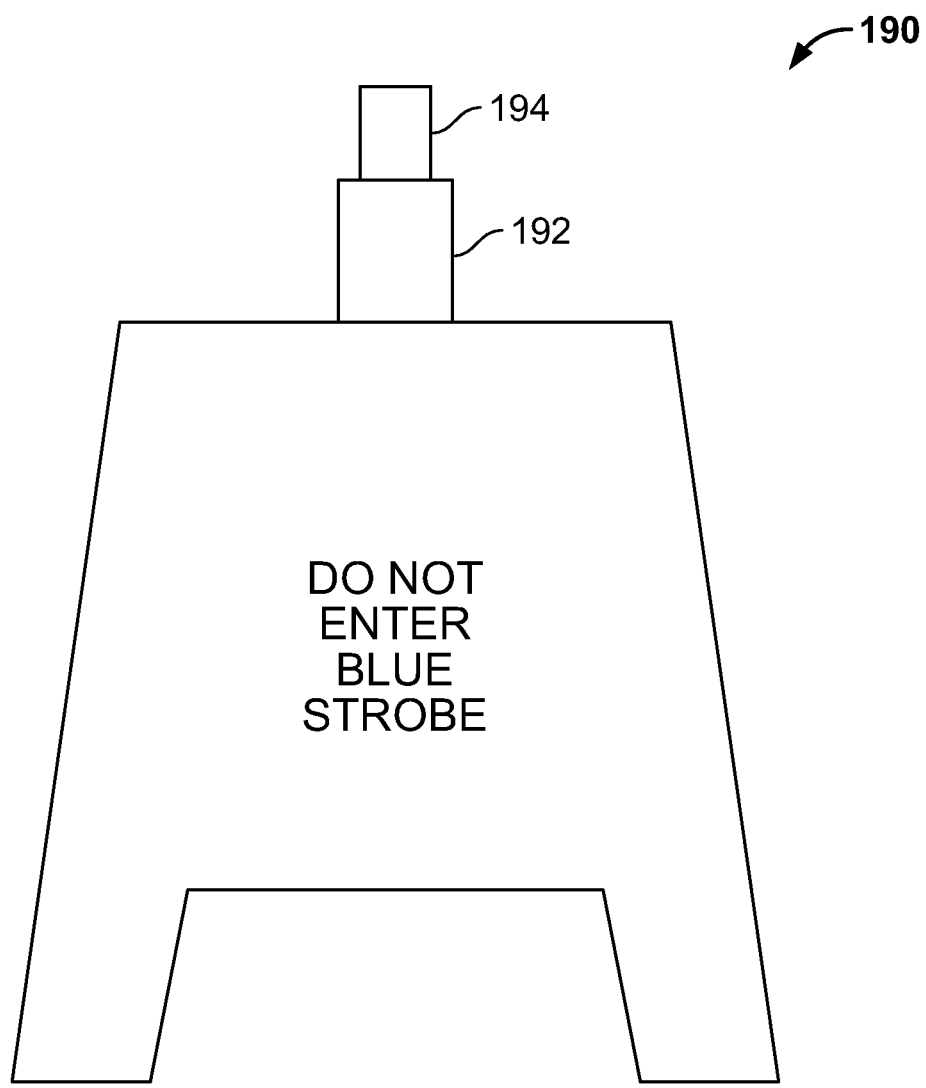
FIG. 9 is a front view of a key card stand that is optionally used with the second embodiment portable decontamination apparatus.

FIG. 9 provides a front view of optional key card stand unit 190. Key card stand unit 190 includes a stand structure 191 and a key card receiver 192 that is adapted for receiving and verifying a key card 194. The purpose of this arrangement is to prevent the unauthorized operation of decontamination unit 110. Only one in possession of key card 194 should be able to activate unit 110. It is also preferable that stand unit 190 also provide a warning to not enter the room where decontamination unit 110 is operating. When key card 194 is inserted in card receiver 192, card receiver 192 transmits a positive signal that is detectable by PLC unit 150 that indicates that the operation of decontamination unit 110 is authorized.

The logic that governs the operation of PLC unit 150 is shown in FIGS. 10A, 10B and 10C, which includes a series of operation sequences, namely an initiation sequence A, an operation sequence B and a shutdown sequence C.

In initiation sequence A, shown in FIG. 10A, PLC unit 150 verifies the following conditions: (a) Key card 192 is inserted into card receiver 192 of key card stand unit 190. (b) Motion detection bypass switch 172 has been activated and that activation occurred a pre-selected period of time in the past. (c) Motion detector 170 is not detecting motion. (d) At least one or two or more of ozone generator board switches 182A, 182B and 182C is or are in the on position. If conditions (a) through (d) are met then the PLC proceeds to operation sequence B. If motion detector 170 is detecting motion, the PLC activates green light 120G in a blinking mode and repeat steps (a) through (d) and then terminates green blinking light 120G when no motion has been detected for a pre-determined period of time.

In operation sequence B, shown in FIG. 10B, the PLC unit does the following: (a) Provides power to axial exhaust fans 144A, 144B and 144C. (b) Provides power to circulation fan 114. (c) Provides power to one or more of ozone generator boards 184A, 184B and 184C as governed by a corresponding combination of switches 182A, 182B and 182C that are in the on position. (d) Provides power to red light 120R to indicate that decontamination unit 110 is operating. (e) Monitors ozone sensor 126 and does the following: (i) When ozone is above 0.1 ppm, provide power to blue strobe light 124 to indicate elevated ozone levels in the space, (ii) if ozone is not above 2.5 ppm after 30 minutes of operation (i.e. not above a predetermined level after a predetermined period of time), turn on red light 120R in a flashing mode and go to shutdown sequence C. (iii) if ozone reaches 4 ppm (i.e. a predetermined desired level), go to shutdown sequence C., and (f) monitors motion sensor 170 during the operation sequence and if motion is detected during the operation sequence, (i) turn on buzzer 128, turn on red light 120R in a flashing mode and go to shutdown sequence C shown in FIG. 10C.

In shutdown sequence C, which is shown in FIG. 10C, the PLC unit does the following: (a) Shuts off power to any ozone generator board 184A, 184B and 184C that is receiving power. (b) Continues to monitor ozone sensor 126 and does the following when ozone falls below 0.1 ppm: (i) Shuts off power to axial exhaust fans 144A, 144B and 144C, (i) shuts off power to circulation fan 114. (iii) Shuts off power to blue strobe light 124. (iv) Turns off red light 120R. (v) Turns on green light 120G in a steady non-blinking mode to indicate completion of decontamination cycle.

As can be seen from the above description, decontamination unit 110 also provides an effective automated apparatus for decontaminating a room 105 of an effective portion of bacteria and viruses that may have been present in room 105. Once activated, decontamination unit 110 is able to disperse sufficient ozone into an enclosed space as noted above such that ozone levels reach 4 ppm within an enclosed space as described above within a reasonable period of time. Once the desired decontaminating ozone level has been reached and the ozone generators have been shut down, ozone levels fall to under 0.1 ppm as the unstable ozone dissipates. The applicants estimate that given an ozone half-life of approximately 20 minutes that returning to such an ozone level that is below 0.1 ppm, from a peak of 4 ppm, would likely occur in less than approximately two hours. A unit such as decontamination unit 110 may be stored and moved easily. Various institutions would be able to deploy sets of such units on a rotating bases. It is believed that such units may be employed to replace at least a substantial portion of the costly and labor intensive deep cleaning that is may now be performed in some high use spaces. Moreover, introducing ozone into an enclosed space at a preselected level, of, for example, 400 ppm is believed to neutralize viruses and bacteria in the air in the space but also on all exposed surfaces, that may be missed during manual disinfectant cleaning operations. Thus, it is the opinion of the applicants that the decontamination units 110 described above provide a safe and effective means for reducing the spread of infectious diseases particularly in heavily used public spaces with reduced labor and costs.

The skilled reader should be mindful that the examples given above and the embodiments described above are for illustrative purposes and are not intended to limit the scope of the invention. It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. A portable decontamination unit for decontaminating an enclosed space, comprising:
   (a) a mobile support structure,
   (b) a recirculation fan mounted to the mobile support structure,
   (c) an ozone generator cabinet mounted to the mobile support structure, the ozone generator cabinet housing (i) at least one ozone generator, (ii) a control unit, (iii) an air intake structure and (iv) at least one exhaust fan, the cabinet also presenting on an external surface thereof a switch in communication with the control unit for activating the decontamination unit and an ozone sensor suitable for detecting the ozone concentration outside the cabinet that is also in communication with the control unit,
   (d) the control unit being programmed to activate the at least one ozone generator, the at least one exhaust fan and the recirculation fan when the switch is in the on position, the control unit further programmed to deactivate the at least one ozone generator when the ozone level in the enclosed space as detected by the ozone sensor reaches a predetermined desired disinfecting level, the control unit further programmed to deactivate the at least one exhaust fan and the recirculation fan when the ozone level detected by the ozone sensor falls below a predetermined low level that is substantially below the desired disinfecting level.

* * * * *